US006433018B1

(12) United States Patent
Siddiqui et al.

(10) Patent No.: US 6,433,018 B1
(45) Date of Patent: Aug. 13, 2002

(54) METHOD FOR REDUCING HYPERTROPHY AND ISCHEMIA

(75) Inventors: Mohammed A. Q. Siddiqui, Basking Ridge, NJ (US); Eduardo Mascareno, Brooklyn; Daniel L. Beckles, Kew Gardens, both of NY (US)

(73) Assignee: The Research Foundation of State University of New York, Albany, NY (US)

( * ) Notice: Subject to any disclaimer, the term of this patent is extended or adjusted under 35 U.S.C. 154(b) by 0 days.

(21) Appl. No.: 09/945,192

(22) Filed: Aug. 31, 2001

(51) Int. Cl.$^7$ ............................................ A61K 31/165
(52) U.S. Cl. ........................................................ 514/619
(58) Field of Search ........................................ 514/619

(56) References Cited

U.S. PATENT DOCUMENTS

| | | | |
|---|---|---|---|
| 5,573,772 A | 11/1996 | Downey et al. | |
| 6,255,296 B1 | 7/2001 | Daniels | |

FOREIGN PATENT DOCUMENTS

| WO | 98/06391 | 2/1998 |
|---|---|---|

OTHER PUBLICATIONS

Alexander Levitzki, "Tyrphostins—Potential Antiproliferative Agents and Novel Molecular Tools," *Biochemical Pharmacology* (1990) 40/5: 913–918.

Shinji Negoro, Keita Kunisada, Erioh Tone, Masanobu Funamoto, Hidemasa Oh, Tadamitsu Kishimoto, Keiko Yamauchi–Takihara, "Activation of JAK/STAT pathway transduces cytoprotective signal in rat acute myocardial infarction," *Cardiovascular Research* (2000) 47: 797–805.

Alexander Levitzki and Aviv Gazit, "Tyrosine Kinase Inhibition: An Approach to Drug Development," *Science* (1995) 267: 1782–1788.

Eduardo Mascareno, Manya Dhar, and M.A.Q. Siddiqui, "Signal transduction and activator of transcription (STAT) protein–dependent activation of angiotensinogen promoter: A cellular signal for hypertrophy in cardiac muscle," *Proc. Natl. Adac. Sci. USA* (1998) 95: 5590–5594.

Naftaly Meydan, Tom Grunberger, Harjit Dadi, Michal Shahar, Enrico Arpaia, Zvi Lapidot, J. Steven Leeder, Melvin Freedman, Amos Cohen, Aviv Gazit, Alexander Levitzki and Chaim M. Roifman, "Inhibition of acute lymophoblastic leukaemia by a Jak–2 inhibitor," *Nature* (1996) 379:645–648.

Alexander Levitzki, "Protein Tyrosine Kinase Inhibitors as Novel Therapeutic Agents," *Pharmacol. Ther.* (1999) 82/2–3: 231–239.

Eduardo Mascareno and M.A.Q. Siddiqui, "The role of Jak/STAT signaling in heart tissue renin–angiotensin system," *Molecular and Cellular Biochemistry* (2000) 212: 171–175.

Domenica Altavilla, Francesco Squadrito, Giuseppe M. Campo, Antonino Saitta, Giovanni Squadrito, Cristina Quartarone, Barbara Deodato, Mariarita Arlotta, Marcella Ferlito, Letteria Minutoli, Michelangelo Tringali, Giuseppe Urna, Aurora Sardella, Achille P. Caputi, "The reduction of myocardial damage and leukocyte polymorphonuclear accumulation following coronary artery occlusion by the tyrosine kinase inhibitor tyrphostin AG 556," *Life Sciences* (2000) 67: 2615–2629.

Stephanie W. Watts, Jennifer A. Florian and Kimberly M. Monroe, "Dissociation of Angiotensin II—Stimulated Activation of Mitogen–Activated Protein Kinase Kinase from Vascular Contraction," *The Journal of Pharmacology and Experimental Therapeutics* (1998) 286/3: 1431–1438.

Shao–Ling Zhang, Catherine To, Xing Chen, Janos G. Filep, Shiow–Shih Tang, Julie R. Ingelfinger, Serge Carrière, John S.D. Chan, "Effect of Renin–Angiotensin System Blockade on the Expression of the Angiotensinogen Gene and Induction of Hypertrophy in Rat Kidney Proximal Tubular Cells," *Experimental Nephrology* (2001) 9: 109–117.

Cindy Ruwhof, Arnoud van der Laarse, "Mechanical stress–induced cardiac hypertrophy: mechanisms and signal transduction pathways," *Cardiovascular Research* (2000) 47: 23–37.

Michael M. Givertz, MD, "Manipulation of the Renin–Angiotensin System," *Circulation* (2001) 104: e14–e18.

Diane H. Boschelli, "Small molecule inhibitors of receptor tyrosine kinases," www.prous.com/journals/dof/sample/html/df240515/df240515.html. Date of publication unknown.

Eduardo Mascareno, PhD; Mohammed El–Shafei, MD; Nilanjana Maulik, Phd; M.Sato, MD; Yueling Guo; Dipak Das, PhD; M.A.Q. Siddiqui, PhD, "JAK/STAT Signaling Is Associated With Cardiac Dysfunction During Ischemia and Reperfusion," *Circulation* (2001) 104:1–5.

DL Beckles, E. Mascareno, and MAQ Siddiqui, "Attenuation of Cardiac Hypertrophy in vivo by Interference with Activation of the Jak/Stat Pathway," presented at the XVII World Congress of the International Society for Heart Research, Winnipeg, Manitoba, Canada (Jul. 6–11, 2001).

*Primary Examiner*—Raymond Henley, III
(74) *Attorney, Agent, or Firm*—Hoffman & Baron, LLP

(57) ABSTRACT

A method is provided for reducing hypertrophy or ischemia to an organ in a mammal. Preferably, the method is used to treat or prevent tissue damage to a human heart. The method includes administering an effective amount of a Jak2 inhibitor, preferably a tyrphostin, such as AG490.

19 Claims, 13 Drawing Sheets

FIG. 1  TRANS AORTIC CONSTRICTION MODEL IN MICE.
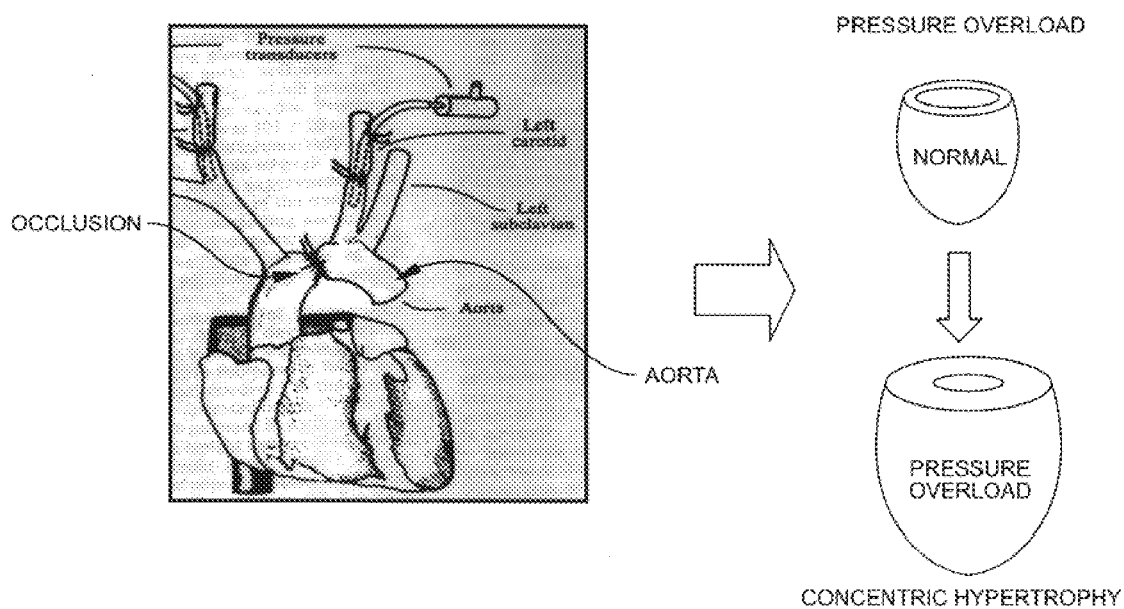

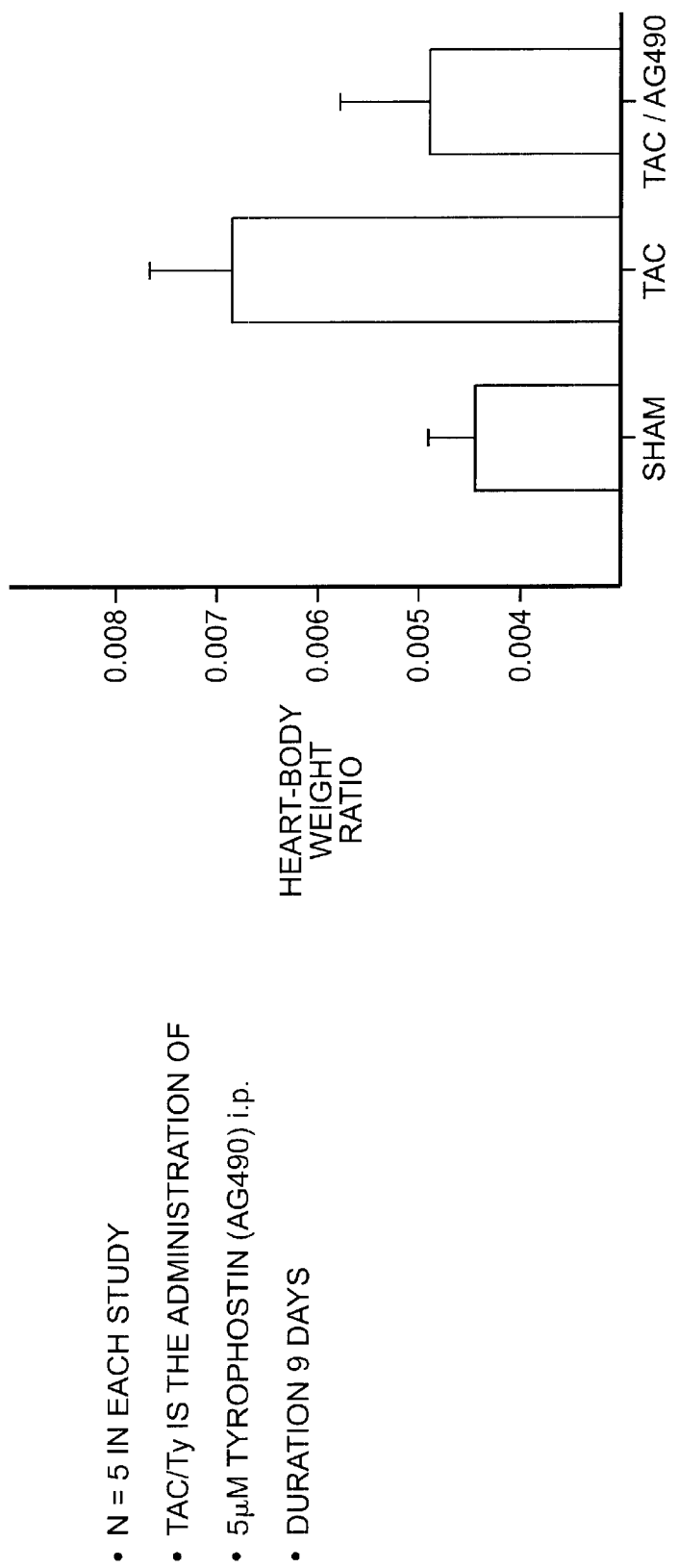
FIG. 2B  EFFECT OF AG490 ON CARDIAC HYPERTROPHY
- N = 5 IN EACH STUDY
- TAC/Ty IS THE ADMINISTRATION OF
- 5μM TYROPHOSTIN (AG490) i.p.
- DURATION 9 DAYS FIG. 3  CARDIAC HYPERTROPHY: NORTHERN BLOT
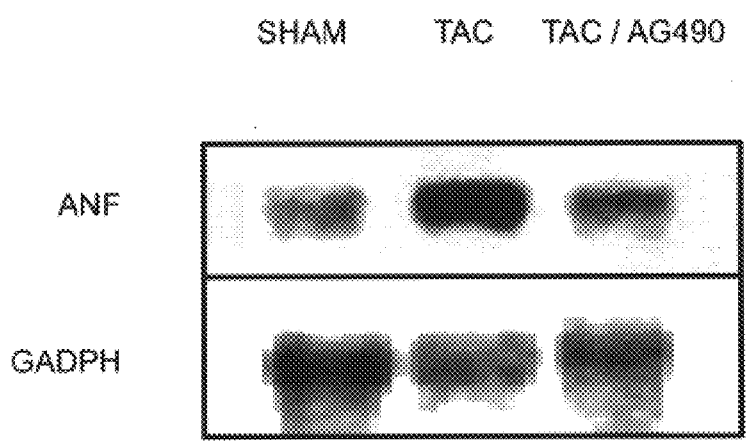

FIG. 5A
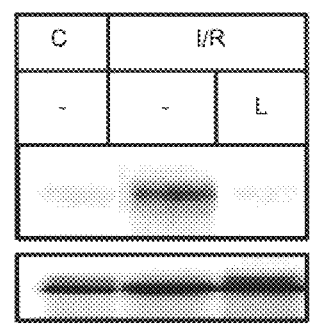
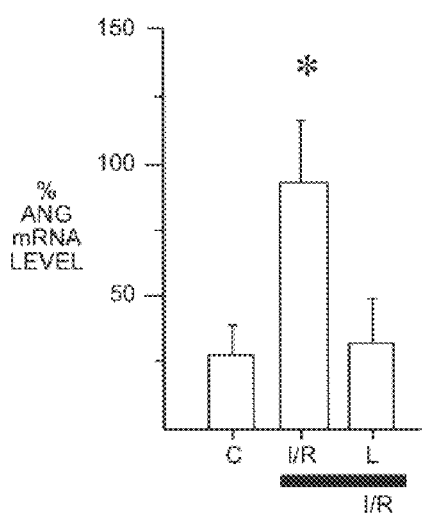

FIG. 5B
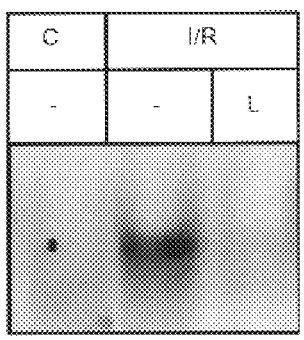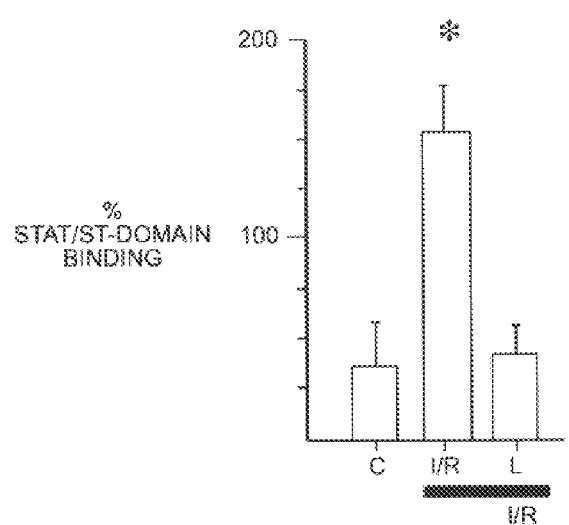

FIG. 6B
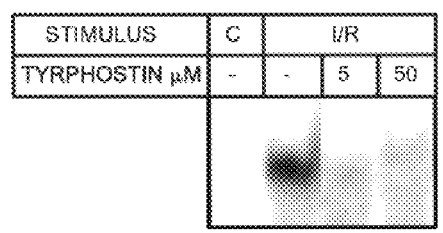
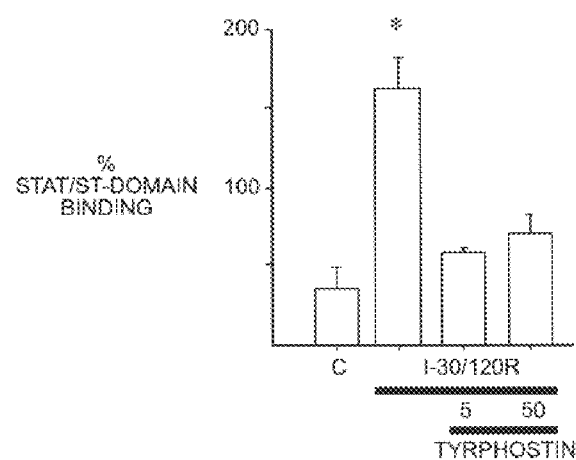

METHOD FOR REDUCING HYPERTROPHY AND ISCHEMIA

This invention was made with Government support under grant awards 5 R01 AR41923-06 and 5 R01 HL53573-06 from the National Institute of Health. The government may have certain rights in this invention.

BACKGROUND OF THE INVENTION

This invention relates to methods for reducing hypertrophy and ischemia.

An increase in the size of the heart (cardiac hypertrophy) in humans is the compensatory response of the myocardium (cardiac muscle) to increased work as a result of an increase in blood pressure or blood volume (hemodynamic overload). The myocardium can increase in size but is not capable of increasing cell number.

Two patterns of hypertrophy can occur depending on the stimulus, either pressure-overloaded hypertrophy or volume-overloaded hypertrophy. Pressure-overloaded hypertrophy typically occurs as a result of hypertension. The ventricles develop concentric hypertrophy, and exhibit an increased ratio of wall thickness to cavity radius.

Volume-overloaded hypertrophy generally occurs as a result of a defect in one of the valves of the heart. The ventricles develop hypertrophy with dilatation (eccentric hypertrophy), resulting in a proportionate increase in ventricular radius and wall thickness.

Initially, the development of cardiac hypertrophy is advantageous since it results in the addition of sarcomeres (contractile units), therefby reducing ventricular wall stress to normal levels (Ruwhof et al., (2000) *Cardio. Res.*, 47:23–37). The increase in the number of sarcomeres leads to augmentation in the overall weight and size of the heart.

With prolonged hemodynamic overload, however, when the hypertrophied heart can no longer meet the increased demand in workload, the heart begins to dilate, stretching the sarcomeres and increasing the force of contraction and stroke volume. The increased stretching of the myocytes further perpetuates the hypertrophy.

Hypertrophy of the myocardium may become increasingly harmful due to the increased metabolic requirements of the enlarged heart. Molecular changes have been observed in the myocytes during development of myocardial hypertrophy. Such changes include the rapid induction of proto-oncogenes and heat shock protein genes, quantitative and qualitative changes in gene expression, and increased rate of protein synthesis (Ruwhof et al., (2000) *Cardio. Res.*, 47:23–37). Changes that occur in the hypertrophied heart may contribute to the development of heart failure. Moreover, ischemic heart disease and arrhythmias may develop, increasing the risk of death.

A different type of heart disease occurs as a result of ischemia. Ischemia is an imbalance between the supply and demand of the heart for oxygenated blood. In addition to insufficient oxygen, ischemia is also caused by a reduced availability of nutrient substrates and inadequate removal of metabolites. In the majority of cases, myocardial ischemia occurs as a result of the narrowing or obstruction of an artery due to atherosclerosis. Four ischemic syndromes may result depending on the rate of development and severity of the arterial narrowing and the myocardial response. The ischemic syndromes are angina pectoris, myocardial infarction, chronic ischemic heart disease, and sudden cardiac death.

The tissue and systemic renin-angiotensin systems play a major role in regulation of pathological cardiovascular functions, such as in hypertension (Raizada et al., (1993) *Cellular and Molecular Biology of the Renin-Angiotensin System*, 515–555), left ventricular hypertrophy (Lavie et al., (1991) *Drugs* 42:945–946), ischemic dilated cardiomyopathy, and heart failure Raynolds et al., (1993) *Lancet* 342:1073–1075). The renin-angiotensin system also exists in other organs and tissues, including the kidneys, prostate, brain, intestines, and the vasculature.

Normal homeostatic levels of a number of hemodynamic properties, such as blood pressure, blood volume, and vascular tone, are maintained by the renin-angiotensin system. Renin is an enzyme that was first isolated from the kidneys over a hundred years ago. Angiotensinogen is cleaved by renin to yield the inactive decapeptide angiotensin I. The vascular endothelium, especially in the lungs, has an enzyme known as angiotensin converting enzyme (ACE) which cleaves off two amino acids to form the octapeptide, angiotensin II.

Angiotensin II is one component of the renin-angiotensin system that is prominently involved in virtually all aspects of the renin-angiotensin activity. The angiotensin II then exerts its effects on target organs and tissues by binding its receptor.

Binding of angiotensin II to its transmembrane domain G-protien coupled receptor ($AT_1$ and/or $AT_2$) can activate several different intracellular signal transduction pathways that use the well-known signal transducers, such as protein kinase A, protein kinase C, MAP kinase, and src (Sadoshima et al., (1993) *Circ. Res.* 73:413–423; Duff et al., (1995) *Cardiovasc. Res.* 30:511–517; Booz et al., (1995) *Cardiovasc. Res.* 30:537–543; Schieffer et al., (1996) *Hypertension* 27:476–480; Bernstein et al., (1996) *Trends Cardiovasc. Med.* 6:179–197).

In addition to these signal transduction pathways, angiotensin II also activates the Janus-associated kinase/signal transducer and activator of transcription (Jak/STAT) pathway. The components of the Jak/STAT pathway are present in a latent state in the cytoplasm of unstimulated cells. Binding of angiotensin II to its receptor leads to activation of Jak, a tyrosine kinase that phosphorylates STAT proteins and allows them to translocate to the nucleus. Within the nucleus, the phosphorylated STAT functions as a transcription factor (Ihle (1996) *Cell* 84:331–334) that recognizes and binds, in a sequence-specific fashion, to cis-regulatory elements in the promoter of target genes.

In mammals, the Jak family consists of Jak1, Jak2, Jak3, and Tyk2. Seven STAT proteins have been identified in mammalin cells, STAT1, STAT2, STAT3, STAT4, STAT5A, STAT5B, and STAT6.

Jaks are crucial components of diverse signal transduction pathways that govern important cellular functions, including cell survival, proliferation, differentiation and apoptosis. Interfering with Jak activity may lead to the loss of a vital signal transduction pathway, thereby disrupting normal cellular processes needed for cell survival. Therefore, it is important to selectively inhibit particular Jaks that are involved in various disease states.

Inhibitors of Jaks include tyrphostins, which are a class of compounds that inhibit protein tyrosine kinases. The tyrosine kinases that are inhibited depends on the substituents that are present on the tyrphostin.

One particular tyrophostin, AG490, selectively inhibits Jak2 and has been proposed for treating cancer (Meydan N, et al. (1996) *Nature* 379:645). Tyrphostin AG556 is a protein tyrosine kinase inhibitor that reduces myocardial damage due to ischemia (Altavilla D., et al, (2000) *Life Sciences* 67:2615). However, the reference does not disclose the molecular mechanism of action of tyrphostin AG556. Furthermore, there is no indication that tyrphostin AG556 is a selective Jak2 inhibitor.

There has been an ongoing search for effective long-term treatments for myocardial dysfunction. Currently, treatments include administering drugs, such as vasiodilators, beta-blockers, free-radical scavengers, and calcium antagonists. Another type of treatment is surgery and includes by-pass surgery and angioplasty. Virtually all of these methods have performed poorly in vivo, and have been ineffective for favorable long-term results.

Cardiovascular disease is the predominant cause of death in all industrialized nations. Diseases such as diabetes, hypertension, myocardial hypertrophy, ischemia and heart failure are on the rise.

Heart muscle cannot currently be regenerated. As a consequence, affected individuals must contend with damaged heart tissue for the rest of their lives. Therefore, restoring normal cardiac function to heart muscles damaged by cardiovascular disease has been a long-term goal of cardiology.

Therefore, there is an immediate need for therapeutic agents that prevent and/or reverse the damage caused by myocardial dysfunction without harming healthy cells.

SUMMARY OF THE INVENTION

These and other objectives have been met by providing a method for reducing hypertrophy of an organ in a mammal at risk for said hypertrophy. The method comprises administering to said mammal an effective amount of a pharmaceutical composition comprising a selective Jak2 inhibitor.

In another embodiment, the invention relates to a method for reducing ischemia of an organ in a mammal at risk for said ischemia. The method comprises administering to said mammal an effective amount of a pharmaceutical composition comprising a selective Jak2 inhibitor.

BRIEF DESCRIPTION OF THE DRAWINGS

FIG. 1: depicts a model for transverse aortic constriction (TAC) in mice.

FIG. 2: depicts cardioprotection of left ventricular hypertrophy (LVH) by tyrphostin AG490. FIG. 2B) Histogram demonstrates a decrease in ratio of heart weight to body weight in tyrphostin AG490 treated animals.

FIG. 3: depicts ANF inhibition by tyrphostin AG490 during cardiac hypertrophy.

FIG. 5: depicts up-regulation of angiotensinogen mRNA during ischemia/reperfusion (I/R) is mediated by STATs. FIG. 5A) Angiotensinogen mRNA is increased during ischemia/reperfusion. FIG. 5B) St-domain/STAT binding activity is increased in hearts subjected to ischemia/reperfusion.

FIG. 6B: depicts reduction of St-domain/STAT binding activity by tyrphostin AG490 in hearts subjected to ischemia/reperfusion.

DETAILED DESCRIPTION OF THE INVENTION

The present invention is based on the discovery by the inventors that a specific signaling pathway is responsible for the onset and maintenance of the renin-angiotensin system in hypertrophy and ischemia. The inventors have discovered that the activation of Jak2, during hypertrophy and ischemia, activates specific STAT proteins, specifically STAT5A and STAT6. Moreover, the inventors have discovered that administration of a Jak2 inhibitor significantly reduces the myocardial damage caused by hypertrophy and ischemia.

Hypertrophy

In one embodiment, the invention relates to a method for reducing hypertrophy of an organ in a mammal at risk for hypertrophy. The method comprises administering to said mammal an effective amount of a pharmaceutical composition comprising a selective Jak2 inhibitor.

Hypertrophy is the enlarging of an organ. The increase in size may, for example, be due to an increase in workload due to some physical defect in the organ itself or one of the biological systems supporting the organ.

Several organs are subject to hypertrophy. Some examples include the heart, kidney, and prostate.

Myocardial hypertrophy, for example, is hypertrophy of the heart, which is typically caused by either myocardial valve damage or high blood pressure. Myocardial hypertrophy may also result from a dilation or expansion of the heart in response to heart muscle damage that causes weak muscle action. Hypertrophic damage may lead, for example, to myocardial infarction, congestive heart failure, and cardiomyopathy.

Left ventricular hypertrophy (LVH) is the medical term for enlargement of the left ventricle of the heart. The left ventricle is the heart's main pumping chamber, and pumps oxygenated blood via the aorta through the systemic circulation.

Figure 2A:
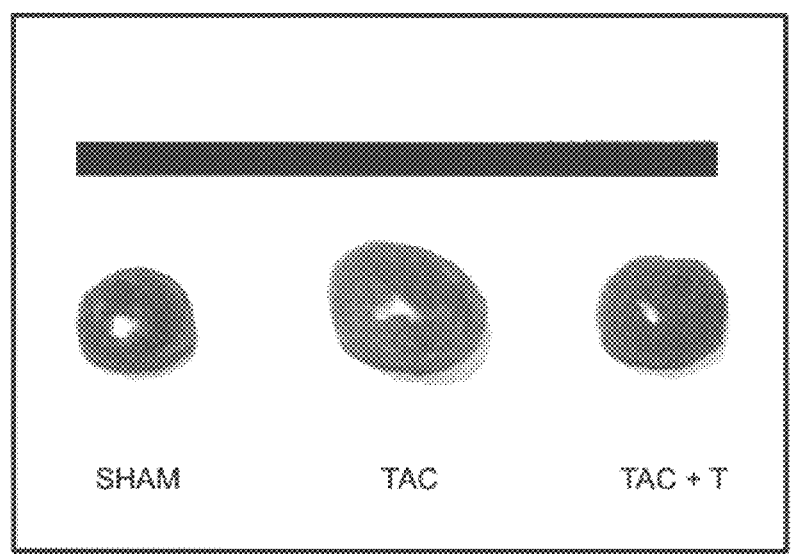
FIG. 2A) Visual inspection of cross section of the heart demonstrates a decrease in LVH in tyrphostin AG490 treated animals.

Hypertrophy may be assessed, for example, by any method known to those skilled in the art. For example, the weight of the organ relative to the body weight of the mammal may be expressed as a ratio, as described in Example 1 and depicted in FIG. 2B.

Ischemia

In another embodiment, the invention relates to a method for reducing ischemia of an organ in a mammal at risk for ischemia. The method comprises administering to said mammal an effective amount of a pharmaceutical composition comprising a selective Jak2 inhibitor.

Ischemia is a deficiency of oxygenated blood. The deficiency of blood may, for example, be caused by functional constriction or obstruction of a blood vessel. The lack of oxygen and/or reduced availability of nutrient substrates and inadequate removal of metabolites may result in tissue damage, for example, apoptosis and/or necrosis of cells.

Several organs are subject to ischemia. Some examples include, but are not limited to, the heart, brain, kidney, and intestines.

Ischemic heart disease is often caused by a reduction in coronary blood flow relative to myocardial demand. The reduction in blood flow may result from a variety of reasons, and typically occurs as a result of atherosclerosis.

As a result of ischemic damage to the heart muscle, the damaged area ceases to contract. Symptoms of such damage include, but are not limited to, cardiac arrhythmias, angina, myocardial infarction, congestive heart failure, and sudden cardiac death.

Ischemia may be assessed by any method known to those skilled in the art. An assessment of ischemic damage may be made, for example, by measuring the infarct (scar) size of the organ, as described in Example 2 and depicted in FIG. 4B.

Other Definitions

In this specification, reducing hypertrophy of an organ means a significant reduction in the size of a hypertrophic organ relative to a healthy organ. Reducing ischemia of an organ means a significant reduction in the infarct size of an ischemic organ. Hypertrophy or ischemia is considered significantly reduced if the size of the hypertrophic organ or the infarct size of the ischemic organ is reduced by at least 10%, preferably at least about 25%, more preferably at least about 50%, even more preferably at least about 75%, and most preferably about 100%.

Any mammal may be treated in accordance with the invention. Mammals include, for example, humans, baboons and other primates, as well as pet animals such as dogs and cats, laboratory animals such as rats and mice, and farm animals such as horses, sheep, and cows.

A mammal at risk for hypertrophy or ischemia may be susceptible for any number or reasons, including a genetic predisposition and/or environmental insult. Some examples of reasons for susceptibility to hypertrophy include, but are not limited to, familial history of high blood pressure, valvular heart disease, and side effects of medication. Valvular heart disease includes, for example, congenital heart disease and rheumatic heart disease. Some examples of reasons for susceptibility to ischemia include, but are not limited to, familial history of atherosclerosis, diet and lifestyle, surgical procedures, and side effects of medication.

Jak2 Inhibitors

A Jak2 inhibitor is any compound that selectively inhibits the phosphorylation of the Jak2 protein in the Jak/STAT pathway. The compound may directly inhibit Jak2, or a component upstream of Jak2. The inhibition of the Jak2 protein must be sufficient to substantially inhibit and preferably prevent the Jak/STAT cascade.

The Jak2 inhibitor may be any type of compound. For example, the compound may be a small organic molecule or a biological compound, such as an antibody or an enzyme.

Examples of Jak2 inhibitors include some members of a class of small organic molecules called tyrphostins. Tyrphostins inhibit the activity of protein tyrosine kinases and have the basic structure shown below:

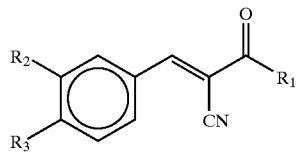

More than one hundred tyrphostins have been synthesized.

The tyrphostin may be any tyrphostin that selectively inhibits Jak2. Some examples of tyrphostins include the various structures described in Meydan et al., (1996) *Nature*, 379:645–648; Levitzki et al, (1995) *Science*, 267:1782–1788; and PCT application WO 98/06391. These structures are incorporated herein by reference.

A preferred class of tyrphostins for use are those wherein:
$R_1 = C_6H_5$—$CH_2$—NH;
$R_2$ and $R_3 =$ H, OH, lower alkyl, F, $NO_2$, $CF_3$, $C_6H_5$—$SO_2$, O—$R_4$, O—CO—$R_4$, or $R_4$
$R_4 =$ phenyl or lower alkyl; and
lower alkyl = $C_1$–$C_4$ branched or unbranched alkyl (for example, methyl or ethyl).

$R_2$ and $R_3$ may be the same or different except $R_2$ and $R_3$ cannot both be H. Preferably, $R_2$ and $R_3$ are OH. The preferred substituent for $R_1$ is $C_6H_5$—$CH_2$—NH. The preferred compound has $R_1 = C_6H_5$—$CH_2$—NH, $R_2 =$ OH, and $R_3 =$ OH. The preferred compound is known as Tyrphostin AG490, which is a selective, specific, and potent Jak2 protein tyrosine kinase inhibitor. The structure of AG490 is shown below:

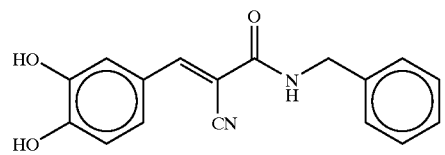

The tyrphostins may be made by methods known in the art, for example, as described in the PCT application WO 98/06391. Briefly, the typhostins may be synthesized by knoevenagel condensation of the appropriate benzaldehyde with malononitrile or the appropriate substituted amide.

A compound is considered a selective inhibitor of Jak2 when the compound inhibits Jak2 activity to an extent significantly greater than it inhibits the activity of other members of the Jak family, e.g., Jak1, Jak3, and Tyk2. Preferably, the selective inhibitor inhibits Jak2 at least 2-fold more than it inhibits other members of the Jak family, more preferably at least about 5-fold more, and most preferably at least about 10-fold more.

Methods for screening for compounds that inhibit members of the Jak family are known in the art. For example, a phosphotyrosine assay is described in Example 5 and depicted in FIG. 6A. See also *Molecular Cloning A Laboratory Manual* by J. Sambrook and D. W. Russel, 2001.

Jak2 inhibitors as defined herein also include pharmaceutically acceptable salts. As used herein, pharmaceutically acceptable salts may be formed by treating the compounds identified above with salt-forming acids and bases which do not substantially increase the toxicity of the compound.

Compositions

In a preferred embodiment, the Jak2 inhibitor is administered in a pharmaceutical composition. The pharmaceutical composition may be manufactured by known means. The pharmaceutical compositions are preferably sterile, non-pyrogenic and isotonic preparations, optionally with one or more of the pharmaceutically acceptable additives listed below.

The pharmaceutical composition may be any composition suitable for pharmaceutical use in a mammal, especially a human. The composition may, for example, be in the form of a solid, a solution, or a suspension.

Pharmaceutical compositions of the Jak2 inhibitors of the invention are preferably stable compositions which may comprise one or more of the following: a stabilizer, a surfactant, preferably a nonionic surfactant, and optionally a salt and/or a buffering agent. The pharmaceutical composition may be in the form of an aqueous solution, or in a lyophilized form.

The stabilizer may, for example, be an amino acid, such as for instance, glycine; or an oligosaccharide, such as for example, sucrose, tetralose, lactose or a dextran. Alternatively, the stabilizer may be a sugar alcohol, such as for instance, mannitol; or a combination thereof. Preferably the stabilizer or combination of stabilizers constitutes from about 0.1% to about 10% by weight of the Jak2 inhibitor.

The surfactant is preferably a nonionic surfactant, such as a polysorbate. Some examples of suitable surfactants include Tween20, Tween80; a polyethylene glycol or a polyoxyethylene polyoxypropylene glycol, such as Pluronic F-68 at from about ) 001% (w/v) to about 10% (w/v), The salt or buffering agent may be any salt or buffering agent, such as for example, sodium chloride, or sodium/potassium phosphate, respectively. Preferably, the buffering agent maintains the pH of the pharmaceutical composition in the range of about 5.5 to about 7.5. The salt and/or buffering agent is also useful to maintain the osmolarity at a level suitable for administration to a human or an animal. Preferably, the salt or buffering agent is present at a roughly isotonic concentration of about 150 mM to about 300 mM.

The pharmaceutical compositions of the present invention may additionally contain one or more conventional additive. Some examples of such additives include a solubilizer such as for example, glycerol; an antioxidant such as for example, benzalkonium chloride (a mixture of quaternary ammonium compounds, known as "quats"), benzyl alcohol, chloretone or chlorobutanol; anaesthetic agent such as for example a morphine derivative; or an isotonic agent etc., such as described above. As a further precaution against oxidation or other spoilage, the pharmaceutical compositions may be stored under nitrogen gas in vials sealed with impermeable stoppers.

An effective amount of a Jak2 inhibitor is the amount which reduces hypertrophy and/or ischemia of the organ. Optimal doses can be determined by those skilled in the art based on a number of parameters including, for example, age, sex, weight, severity of the condition being treated, the compound being administered, and the route of administration. For example, an effective amount of Jak2 inhibitor can be that amount that would produce a blood serum volume level of between about 0.01 $\mu$M to about 50 $\mu$M, preferably between about 1.0 $\mu$M to about 5 $\mu$M.

Administration

The Jak2 inhibitor can be administered by any suitable method, as is known in the art. For example, the Jak2 inhibitor can be administered topically or systemically. Systemic administration is preferred. Adminstration using controlled release delivery systems, as is known in the art, is also contemplated herein.

Systemic administration includes both parenteral and enteral routes. For example, Jak2 inhibitors such as tyrphostins can easily be administered intravenously, which is a preferred route of delivery. Intravenous administration can be accomplished by mixing the Jak2 inhibitor in a suitable pharmaceutical carrier (vehicle) or excipient as understood by practitioners in the art.

Oral or enteral administration includes, for example, formulations such as tablets, capsules, pills, troches, elixirs, suspensions, syrups, wafers, chewing gum and the like.

The Jak2 inhibitor may be administered as a protective agent before hypertrophy and/or ischemia occurs. For example, the Jak2 inhibitor may be used as a prophylactic treatment to prevent hypertrophy and/or ischemia in a mammal at risk for hypertrophy and/or ischemia.

In a further embodiment, the Jak2 inhibitor may be administered at a time after the hypertrophy and/or ischemia occurs in order to minimize and/or reverse the hypertrophy and/or ischemia, as well as to prevent further damage resulting from hypertrophy and/or ischemia. When administering the Jak2 inhibitor after hypertrophy and/or ischemia has occurred, it is preferred that the Jak2 inhibitor be administered as soon thereafter as possible. Jak2 can also be administered while the hypertrophy and/or ischemia is occurring.

Without being bound by theory, it is believed that the methods of the invention described can inhibit the activation of Jak2 and therefore interfere with the maintenance of the autocrine loop of the renin-angiotensin system, thereby acting as a protective agent.

EXAMPLE 1

This example demonstrates cardioprotection from left ventricular hypertrophy by Tyrphostin AG 490.

Pressure overload was produced by transverse aortic constriction (TAC) to induce left ventricular hypertrophy (FIG. 1). Briefly, male C57/BL6 mice, weighing 20 to 24 grams, were anesthetized by intra-peritoneal injection of a cocktail of ketamine (100 mg/kg) and xylazine (5 mg/ml). The mice were shaved, restrained, and orally intubated (under direct vision via a vertical cervical incision) using a 22 guage blunt feeding needle. Respiration was artificially controlled (tidal volume of 0.1 to 0.3 ml) at a respiratory rate of 110 to 150 breaths/minute using a ventilator (Harvard Apparatus Rodent Ventilator, model 683). A median stemotomy was performed and the sternum retracted. The thymus was retracted anteriorly and the aortic arch identified and ligated (using 8.0 nylon suture; Ethicon) between the innominate and left common carotid artery with an overlying 27-guage needle; and then the needle removed to leave a discrete region of stenosis. The chest was then closed in two layers (using 6.0 vicryl suture, Ethicon) and the pneumothorax evacuated. Some mice were subjected to a sham operation in which the aortic arch was visualized but not banded. The mice were then extubated and monitored post-op for 3 to 12 hours. The survival rate at the end of the learning period is greater than 90%.

Figure 2C:
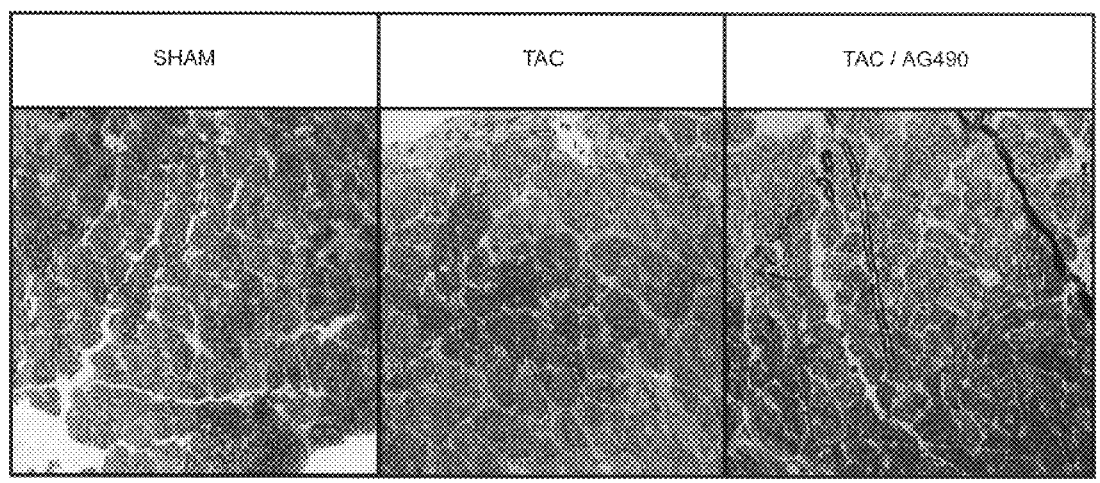
FIG. 2C) Light microscopy of cardiomyocytes of left ventricle demonstrates a decrease in hypertrophy in tyrphostin AG490 treated animals.

Nine days post-op, the hearts were removed from heparinized (500 U) mice and euthanized with a lethal dose of pentobarbital (150 mg/kg). The hearts were analyzed by visual inspection of a cross-section of the heart (FIG. 2A), determination of heart to body weight ratio (FIG. 2B), and light microscopy of the cardiomyocytes in the left ventricular (FIG. 2C), and activation of artiel natuiretic factor (ANF), a specific molecular marker for hypertrophy (FIG. 3). Based on these determinations, all trans-aortic constricted mice developed well-defined left ventricular hypertrophy.

To determine whether tyrphostin AG490 could reverse the hypertrophy induced by traverse aortic constriction, tyrphostin AG490 (5 $\mu$M) was administered to the mice, intra-peritoneal, 24 hours before being subjected to transverse aortic constriction and every 24 hours thereafter for the duration of the study (9 days). Chronic administration of tyrophostin AG490 caused a remarkable reversal of hypertrophy (see FIGS. 2A, 2B, 2C, and 3).

EXAMPLE 2

This example demonstrates that administration of Jak2 afforded cardioprotection against ischemia-induced changes in myocardial performance by inhibition of Jak2.

Figure 4A:
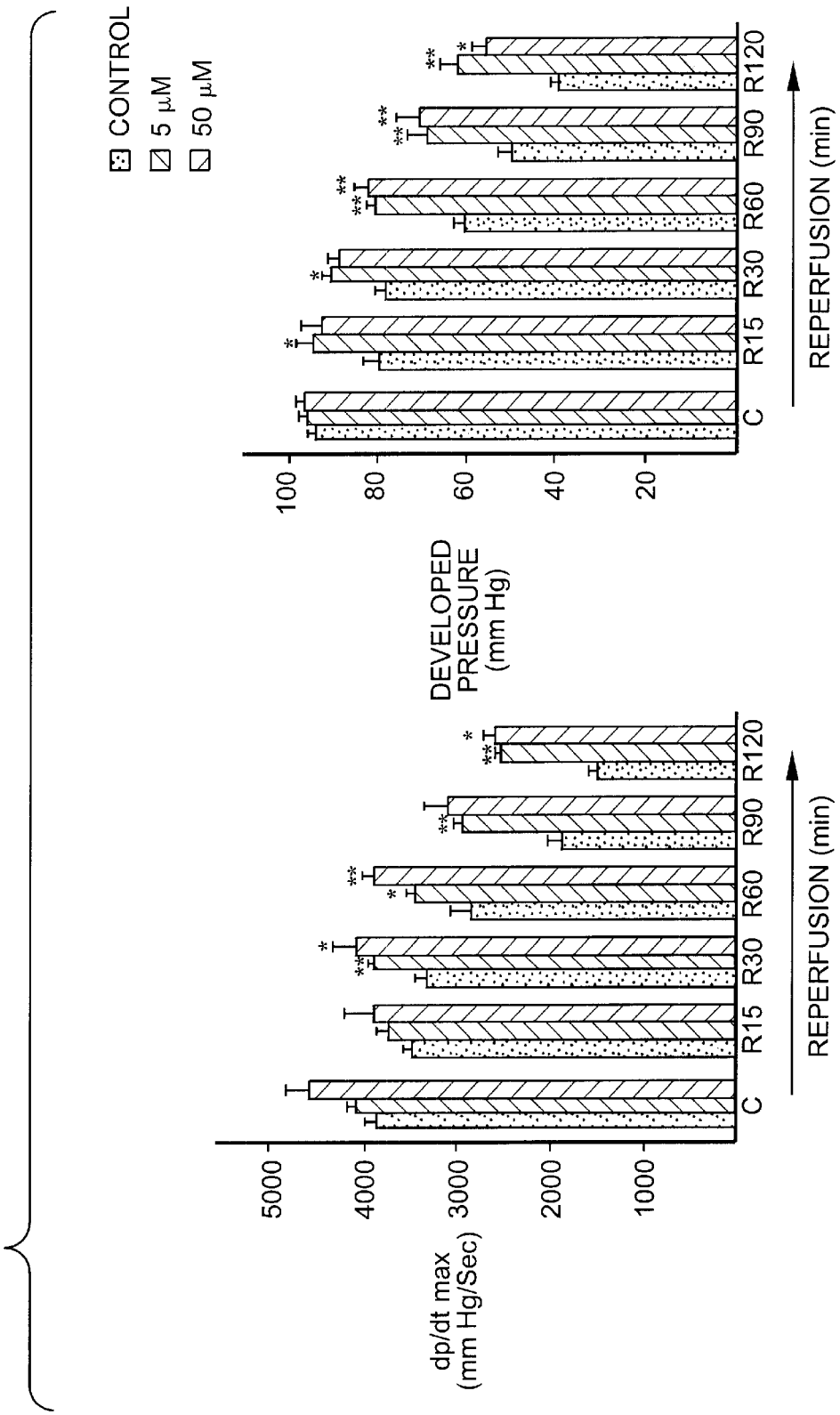
FIG. 4A: depicts the effects of tyrphostin AG490 on myocardial function.
Figure 4B:
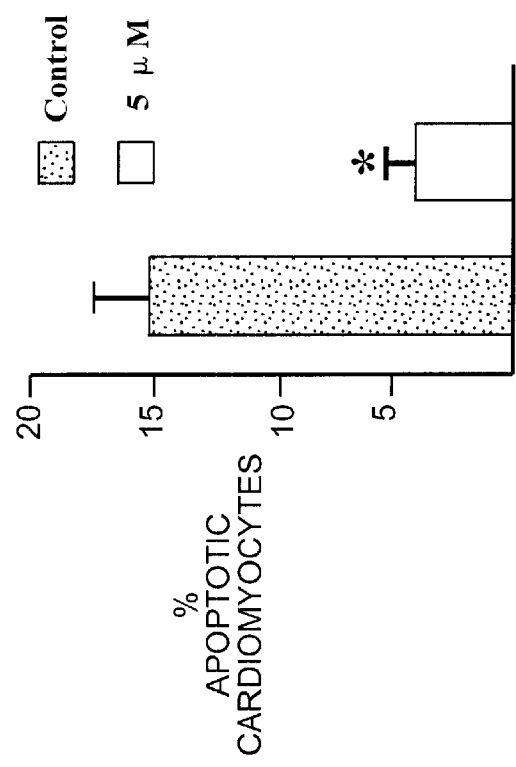
FIG. 4B: depicts reduction of infarct size by tyrphostin AG490 during ischemia/reperfusion.

Using spontaneously beating working hearts that were not paced, the absolute values and the first derivative of developed pressure were progressively decreased with reperfusion, as expected (FIG. 4A). The inhibitor, tyrphostin AG490, at both 5 and 50 μmol/L, was able to provide cardioprotection to approximately the same degree. This was particularly true during the first 60 min. of reperfusion, when the dP/dt value was not lowered, and developed pressure was minimally lowered, in the treated groups. The baseline value for dP/dt increased slightly in high (50 μmol/L) concentrations of tyrphostin AG490. In addition, the slopes of the decay for the treated and untreated groups after 60 min. were similar. The values for both dP/dt and developed pressure in all treated groups were significantly higher than in the untreated group. Developed pressure was notably higher in the tyrphostin groups subjected to 60 min. of reperfusion, R-60 (86±2.5 and 86±4.8 compared with 64±3.2 mm Hg); 90 min. of reperfusion, R-90 (69±5 and 72.7±5.7 compared with 46±3 mm HG); and 120 min. of reperfusion, R-120 (60.85±4 and 53.75±7 compared with 38.66±2 mm Hg). dp/dt values were markedly higher in groups at both concentrations throughout most of the reperfusion period compared with the control reperfused group, the difference being apparent at R-30 (3818±49.46 and 4156±238 versus 3382±68.8), R-60 (3362±53.14 and 3840±140 versus 2878±237), R-90 (2840±88 and 3194.7±228 versus 1842±162), and R-120 (2552±58.9 and 2626±269 versus 1543±94).

To gain insight into the physiological basis for cardioprotection afforded by tyrphostin AG490, the extent of cardiomyocyte infarct size and apoptosis were measured. On termination of treatment with tyrphostin AG490, hearts were immersed in 1% triphenyl tetrazolium solution in phosphate buffer ($Na_2HPO_4$ 88 mmol/l, $NaH_2PO_4$ 1.8 mmol/l) for 10 min. at 37° C. and stored at −70° C. for processing. Frozen hearts (ventricular tissue) were sliced transversely in a plane perpendicular to the apicobasal axis into 0.5 mm thick sections, blotted dry, placed between microscope slides, and scanned on a Hewlett-Packard Scanjet 5p single-pass flatbed scanner. With the NIH 1.61 image processing software, each digitized image was subjected to equivalent degrees of background subtraction, brightness, and contrast enhancement for improved clarity and distinctness. Risk (equivalent to total left ventricular muscle mass) and infarct zones of each slice were traced, and the respective areas were calculated in terms of pixels. The weight of each slice was then recorded to facilitate the expression of total and infarct masses of each slice in grams. The risk and infarct volumes of each slice in cubic centimeters were then calculated on the basis of slice weight to correct for any errors due to nonuniformity of heart slice thickness. The risk volumes and infarct volumes of each slice were summed to obtain the risk and infarct volumes for the whole heart. Infarct size was taken to be the percent infarct volume/risk volume for any one heart.

Immunohistochemical detection of apoptotic cells was carried out by use of terminal dUTP nick end-labeling (TUNEL), in which residues of digoxigenin-labeled dUTP are catalytically incorporated into the DNA by terminal deoxynucleotidyl transferase II. The cells were incubated with a sheep polyclonal anti-digoxigenin antibody followed by a FITC-conjugated rabbit anti-sheep IgG as a secondary antibody. The heart sections were washed in PBS 3 times, blocked with normal rabbit serum, and incubated with mouse monoclonal antibody recognizing cardiac myosin heavy chain (Biogenesis Ltd) followed by staining with TRIRC-conjugated rabbit anti-mouse IgG (200:1 dilution, Dako, Japan). The fluorescence staining was viewed with a confocal laser microscope (Olympus Co). The apoptoic cells were counted and expressed as percentage of total myocyte population.

Figure 4C:
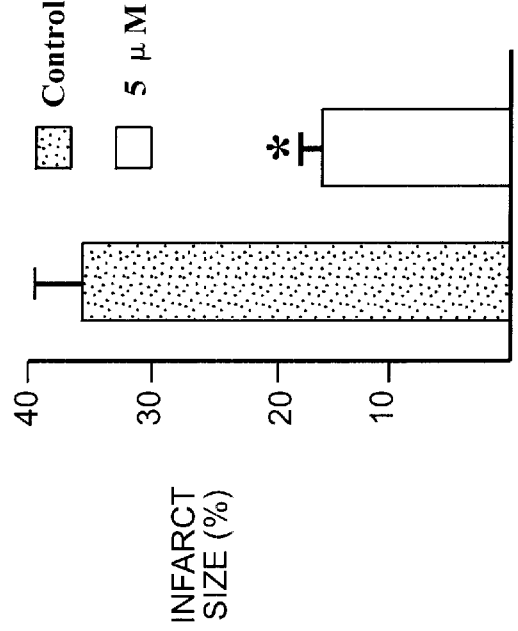
FIG. 4C: depicts reduction of apoptosis of cardiomyocytes by tyrphostin AG490 during ischemia/reperfusion.

Administration of tyrphostin AG490 reduced myocardial infarct size (FIG. 4B) and caused a marked lowering of apoptotic cell death (FIG. 4C), thereby, attributing, at least in part, to the recovery of contractile function upon treatment with tyrphostin AG490.

EXAMPLE 3

This example demonstrates upregulation of rat heart angiotensinogen mRNA during ischemia/reperfusion.

Ischemia was induced by a modified Langendorf-reperfusion method in rat hearts. Hearts from adult male rats were randomly divided into 4 groups and subjected to ischemia/reperfusion. In the ischemic group, hearts were perfused with Krebs-Henseleit buffer for 60 minutes, followed by 30 minutes of global ischemia. In the ischemic/reperfused group, hearts were perfused for 60 minutes, followed by 30 minutes of global ischemia and 120 minutes of reperfusion. Control group hearts were perfused for the same lengths of time.

Rat hearts subjected to ischemia/referfusion were tested to determine whether activation of the renin-angiotensin system, as reflected by an increase in angiotensinogen mRNA, occurs in ischemic injury. The level of angiotensinogen mRNA was analyzed by primer extension assay using gene-specific DNA probes. A DNA primer spanning the complementary sequence of the rat angiotensinogen cDNA between nucleotides 302 and 279 (5'-AGGAGATGAAAGGGGTGGATGTAT-3') was end-labeled and used to evaluate the expression of angiotensinogen mRNA in total RNA isolated from the rat heart. The primer extension protocol was performed according to instructions provided by the supplier (Progema). Rat GAPDH cDNA specific primer was used as control. There was a marked increase in mRNA level after 30 minutes of ischemia and 120 minutes of reperfusion (FIG. 5A). The increase in mRNA was sensitive to blockage of the $AT_1$, receptor, because pretreatment with losartan (L) reduced it almost entirely to the level of the control sample (C). The levels of the ribosomal marker L32 mRNA, used as control, remained unchanged.

EXAMPLE 4

This example demonstrates STAT activation during ischemia/reperfusion.

Nuclear extracts were examined in hearts subjected to global ischemia to determine whether there is enhanced STAT binding activity to the St domain of the angiotensinogen promoter. The nuclear heart extracts were examined by the electrophoretic gel mobility-shift assay that exployed the use of the chemically synthesized oligonucleotide sequence of the St domain. The St-domain DNA probe for protein binding was a double-stranded oligonucleotide containing the sequence 5'-GGGTtcCTGGAAGGG-3' and complementary strand 5'-CCCTTCCAGgaACCC-3', respectively. These probes were end-labeled by polynucleotide kinase and [$\gamma$-$^{32}$P]ATP. Binding reaction mixture containing 0.5 ng of labeled DNA (1,000 cpm), 2 μg of poly(dI-C), and 1–12 μg of protein in buffer containing 20 MM Hepes, 3% glycerol, 1.5 mM $MgCl_2$, 1 mM DTT, 2 mM EDTA and 50 mM KCl, pH 7.5 was allowed to incubate at 4° C. for 30 min. The reactions were analyzed by electrophoresis on 8% polyacrylamide gel in 0.375×TBE (0.33 mM Tris borate, pH 8.7 and 1.0 mM EDTA). After electrophoresis, the gels were dried and subjected to autoradiography. There was a strong St-domain/STAT binding activity in the hearts subjected to 30 min. ischemia/120 min.

reperfusion, which was almost entirely abolished in losartan-treated heart, suggesting that losartan (L) treatment during perfusion resulted in loss of the activated STAT participation in complex formation. (FIG. 5B). The activation of STATs and the consequent binding to the St-domain in the angiotensinogen promoter accounts for the increase in transcription of angiotensinogen mRNA. Thus, the loss of STAT/DNA interaction and the reduction in the angiotensinogen mRNA levels (see FIG. 5A) due to losartan treatment appear to be correlative.

Figure 5C:
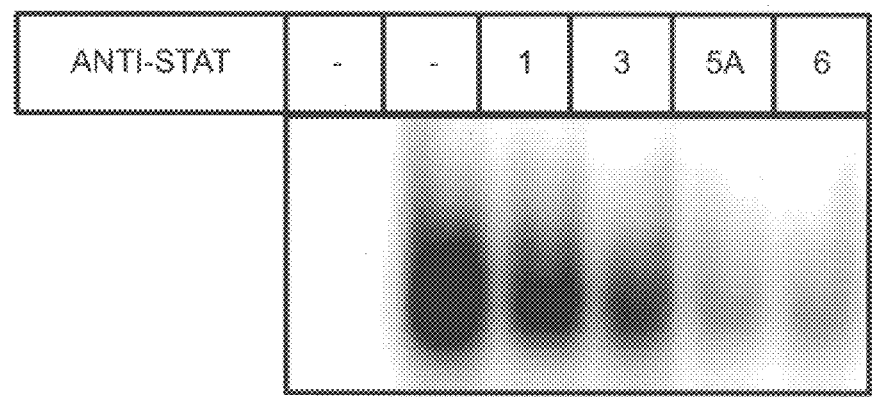
FIG. 5C) STAT5A and STAT6 are activated in ischemic hearts.

To identify the STAT proteins that were activated in the ischemic hearts, nuclear extracts were preincubated for 30 min with polyclonal antibodies against STAT1, STAT3, STAT5A, and STAT6 before adding the St-domain DNA labeled probe. Examination of the reaction by gel mobility-shift assay showed that STAT5A and STAT6 DNA complexes were prominently disrupted by antibodies against STAT5A and STAT6 (FIG. 5C). Therefore, STAT5A and STAT6 are activated in ischemic hearts.

EXAMPLE 5

This example demonstrates the effect of Jak2 inhibition on STAT/DNA binding and angiotensinogen mRNA.

Figure 6A:
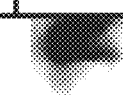
FIG. 6A: depicts Jak2 inhibition by tyrophostin AG490 during ischemia/reperfusion (I/R).

Rats were pretreated with 5 or 50 $\mu$mol/L of tyrphostin AG490 24 h prior to ischemia/reperfusion followed by chronic administration of tyrphostin AG490 during the process of ischemia/reperfusion. A phosphotyrosine assay was performed. Briefly, nuclear extracts from hearts subjected to ischemia/reperfusion in presence of absence of tyrphostin AG490 were immunoprecipitated with anti-phosphotyrosine antibodies (4G10). Fifty microliters of 50% protein A-agarose, prewashed in lysis buffer (Upstate Biotechnology) was then added and the mixture was incubated for 2 hr at 4° C. Each sample was washed with washing buffer containing 150 mM NaCl, 50 mM Tris-HCL (pH 7.4), 5 mM EDTA, 0.25% Triton X-100, 2 mM phenylmethylsulfonyl fluoride, aprotinin (0.2 unit/ml), 1 mM $Na_3VO_4$, and 1 mM NaF. Samples were eluted in 2X Laemmli's sample buffer. Proteins were separated on a 7.5% SDS/polyacrylamide gel and transferred to nitrocellulose membrane, Nitropure (Micron Separations, Westboro, Mass.). Blots were probed with polyclonal antibody against Jak2 and developed according to the chemiluminescence protocol. Administration of tyrphostin AG490 in perfusion medium was inhibitory at both 5 and 50 lmol/L for phosphorylation of Jak2, which was activated readily in the ischemic heart in absence of the inhibitor (FIG. 6A).

Figure 6C:
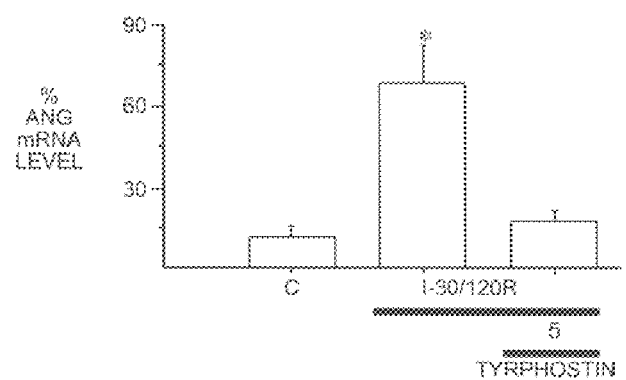
FIG. 6C: depicts inhibition of angiotensinogen mRNA by tyrphostin AG490 in hearts subjected to ischemia/reperfusion.

When extracts from the same hearts were examined by gel mobility-shift assay for DNA binding, there was a total loss of STAT/DNA complex formation in the tyrphostin AG490 treated hearts (FIG. 6B). Treatment with tyrphostin AG490 also inhibited the stimulation of the angiotensinogen mRNA level that was observed in the ischemic tissues in absence of the inhibitor (FIG. 6C). These results therefore strongly suggest that activation of the Jak/STAT pathway, increases in the STAT/angiotensinogen promoter binding activity, and the upregulation of angiotensinogen mRNA all are casually related.

We claim:

1. A method for reducing hypertrophy of an organ in a mammal at risk for said hypertrophy comprising administering to said mammal an effective amount of a pharmaceutical composition comprising a selective Jak2 inhibitor.

2. A method as set forth in claim 1 wherein said Jak2 inhibitor is a tyrphostin.

3. A method as set forth in claim 2 wherein said tyrphostin is Tyrphostin AG490.

4. A method as set forth in claim 1 wherein said organ is the heart.

5. A method as set forth in claim 1 wherein said mammal is human.

6. A method as set forth in claim 1 wherein said administration of the Jak2 inhibitor is systemic.

7. A method as set forth in claim 1 wherein said composition is administered before, while or after damage from said hypertrophy occurs.

8. A method as set forth in claim 1 wherein said effective amount is an amount that produces a blood serum volume level of between about 0.01 $\mu$M to about 50 $\mu$M.

9. A method as set forth in claim 8 wherein said effective amount is an amount that produces a blood serum volume level preferably between about 1 $\mu$M to about 5 $\mu$M.

10. A method as set forth in claim 1 wherein said hypertrophy is left ventricular hypertrophy.

11. A method for reducing ischemia of an organ in a mammal at risk for said ischemia comprising administering to said mammal an effective amount of a pharmaceutical composition comprising a selective Jak 2 inhibitor.

12. A method as set forth in claim 11 wherein said Jak2 inhibitor is a tyrphostin.

13. A method as set forth in claim 12 wherein said tyrphostin is Tyrphostin AG490.

14. A method as set forth in claim 11 wherein said organ is the heart.

15. A method as set forth in claim 11 wherein said mammal is human.

16. A method as set forth in claim 11 wherein said composition is administered before, while or after damage from said ischemia occurs.

17. A method as set forth in claim 11 wherein said administration of the Jak2 inhibitor is systemic.

18. A method as set forth in claim 11 wherein said effective amount is an amount that produces a blood serum volume level of between about 0.01 $\mu$M to about 50 $\mu$M.

19. A method as set forth in claim 18 wherein said effective amount is an amount that produces a blood serum volume level preferably between about 1 $\mu$M to about 5 $\mu$M.

* * * * *

UNITED STATES PATENT AND TRADEMARK OFFICE
CERTIFICATE OF CORRECTION

PATENT NO. : 6,433,018 B1
DATED : October 16, 2002
INVENTOR(S) : Siddiqui et al.

It is certified that error appears in the above-identified patent and that said Letters Patent is hereby corrected as shown below:

<u>Title page,</u>
Item [74], now reads "Hoffman & Baron, LLP" should read -- Hoffmann & Baron, LLP --

<u>Column 10,</u>
Line 60, now reads "MM Hepes, 3%" should read -- mM Hepes, 3% --

Signed and Sealed this

Fourth Day of February, 2003

JAMES E. ROGAN
*Director of the United States Patent and Trademark Office*